US00PP28006P2

(12) United States Plant Patent
Probst

(10) Patent No.: US PP28,006 P2
(45) Date of Patent: May 9, 2017

(54) ***COREOPSIS* PLANT NAMED 'STARSTRUCK'**

(50) Latin Name: ***Coreopsis* hybrid**
Varietal Denomination: Starstruck

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 94 days.

(21) Appl. No.: 14/545,259

(22) Filed: Apr. 13, 2015

(51) Int. Cl.
*A01H 5/02* (2006.01)

(52) U.S. Cl.
USPC ..... Plt./417

(58) Field of Classification Search
USPC ..... Plt./417
See application file for complete search history.

(56) References Cited

PUBLICATIONS

Emerald Coast Growers Oct. 10, 2014, retrieved on Aug. 18, 2016, retrieved from the Internet at <http://spotidoc.com/doc/318831/emerald-coast-growers-oct.-10--2014> p. 6.*

Pioneer Gardens, Inc. 2014-2015 Program and Availability retrieved on Aug. 18, 2016, retrieved from the Internet at <https://nebula.wsimg.com/a8e14aaf5f2c1ab73574f0980ec0bb03?AccessKeyId=D4DC3ED90C9EAD58C2B4&disposition=0&alloworigin=1> Aug. 27, 2014, pp. 1-20.*

* cited by examiner

*Primary Examiner* — June Hwu

(74) *Attorney, Agent, or Firm* — Penny J. Aguirre

(57) ABSTRACT

A new cultivar of hybrid *Coreopsis* named 'Starstruck' characterized by its compact plant habit, its floriferous and long bloom season that does not require deadheading, its nearly sterile, large inflorescences with ray florets that are white in color with a large purple eye that expands to cover the surface of the ray florets in cooler temperatures, its cold hardiness at least to U.S.D.A. Zone 5a, and its resistance to powdery mildew and leaf spot.

2 Drawing Sheets

Botanical classification: *Coreopsis* hybrid.
Variety denomination: 'Starstruck'.

BACKGROUND OF THE INVENTION

The present invention relates to a new and distinct cultivar of a plant botanically of hybrid origin and known as *Coreopsis* 'Starstruck'. The new cultivar will be referred to hereafter by its cultivar name 'Starstruck'. 'Starstruck' is an herbaceous perennial grown for landscape and container use.

The new invention arose from an ongoing controlled breeding program in New Braintree, Mass. The objective of the breeding program is to develop hybrid cultivars of *Coreopsis* with unique and superior garden attributes. In particular, to develop long-lived cultivars in a wide range of flower colors and plant forms that are sturdy, exhibit a true perennial habit, and are cold hardy to at least U.S.D.A Zone 5a.

The Inventor made a controlled cross in August of 2011 in his test garden in New Braintree, Mass. between an unnamed proprietary *Coreopsis* plant from the Inventor's breeding program, reference no. I 10-31, as the female parent (not patented) and pollen that was pooled from a variety of unnamed, proprietary plants (not patented) from his breeding program as the male parents (all nearly sterile). The exact male parentage is therefore unknown. 'Starstruck' was selected in September of 2012 as a single unique plant amongst the resulting seedlings.

Asexual propagation of the new cultivar was first accomplished under the direction of the Inventor by stem cuttings in Kensington, Conn. in September of 2012. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Starstruck' as unique cultivar of *Coreopsis*.

1. 'Starstruck' exhibits a compact plant habit reaching an average of 33 cm in height and 60 cm in width.
2. 'Starstruck' exhibits a floriferous and long bloom season that does not require deadheading, beginning in late-June and lasting until frost in Kensington, Conn.
3. 'Starstruck' exhibits nearly sterile, large inflorescences with ray florets that are white in color with a large purple eye that expands to cover the surface of the ray florets in cooler temperatures.
4. 'Starstruck' exhibits cold hardiness at least to U.S.D.A. Zone 5a.
5. 'Starstruck' exhibits resistance to powdery mildew (*Podosphaera macularis*) and leaf spot (*Pseudomonas cichorii*).

The female parent of 'Starstruck' differs from 'Starstruck' in being taller in plant height, in having very fertile flowers causing a shorter bloom season due to seed set. 'Starstruck' can be most closely compared to *Coreopsis* cultivars 'Star Cluster' (U.S. Plant Pat. No. 23,035) and 'Snowberry' (U.S. Plant Pat. No. 18,560). 'Star Cluster' is similar to 'Starstruck' in being resistant to powdery mildew and leaf spot and in having a long bloom season that does not require deadheading. 'Star Cluster' differs from 'Starstruck' in being taller in height, in having inflorescences that are smaller in size, and in having white ray florets with a small basal blotch that is purple in color (rather than a purple eye zone). 'Snowberry' is similar to 'Starstruck' in having ray florets that are white and purple in color. 'Snowberry' differs from 'Starstruck' in being susceptible to powdery mildew, in having a taller plant height, and in having inflorescences that are much smaller in size with ray florets that are white in color with a small magenta eye.

BRIEF DESCRIPTION OF THE DRAWINGS

The accompanying colored photographs illustrate the overall appearance and distinct characteristics of the new *Coreopsis*.

The photograph in FIG. 1 was taken of a plant three months in age (from a 30-cell plug) as grown outdoors in a one-gallon container in Kensington, Conn. and provides a side view of a plant of 'Starstruck' in bloom.

Figure 1:
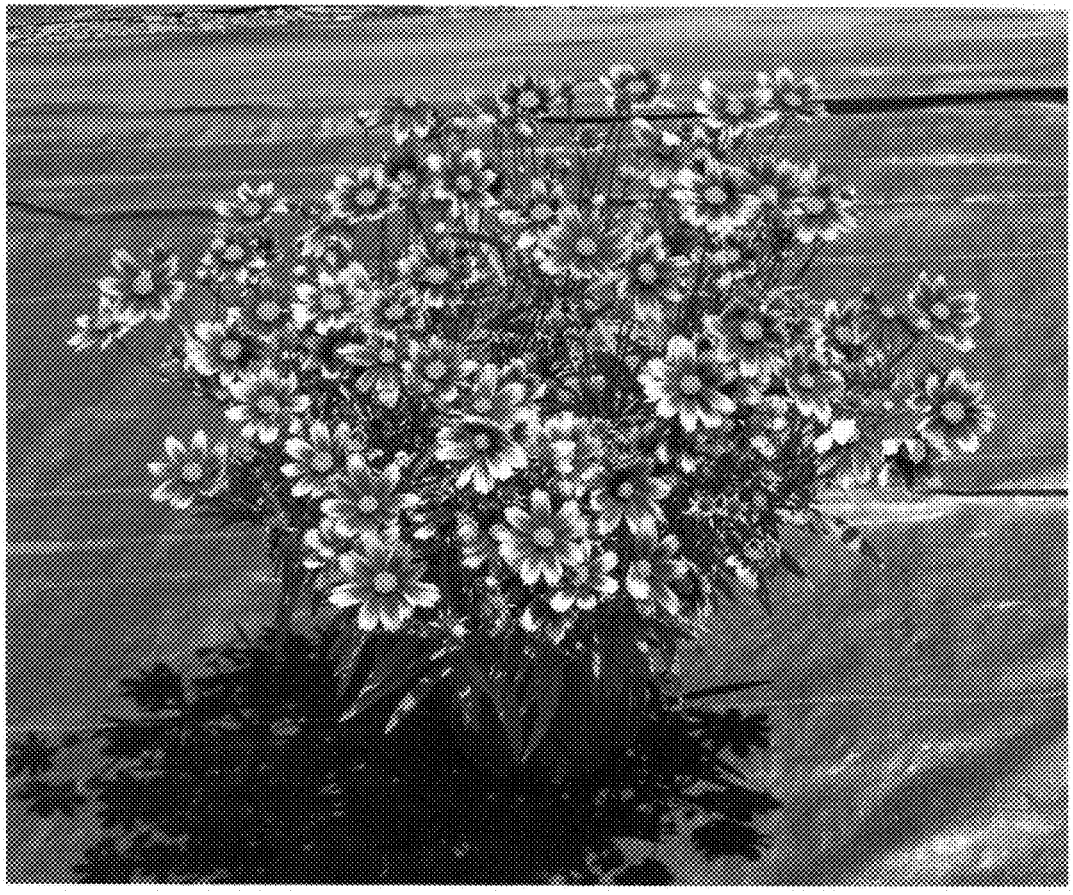
Figure 2:
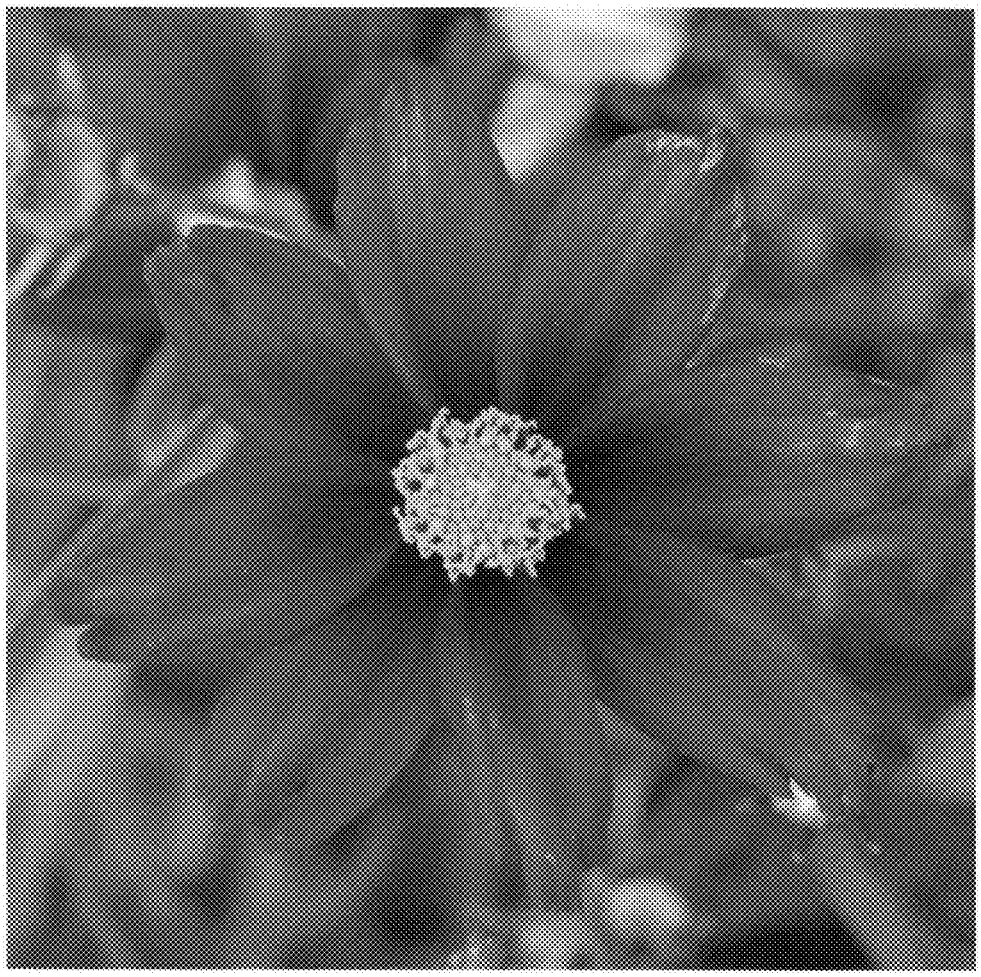

The photograph in FIG. 2 was taken of a plant five months in age as grown in the ground in New Braintree, Mass. and provides a close-up view of an inflorescence of 'Starstruck' during cooler temperatures.

The colors in the photographs are as close as possible with the photographic and printing technology utilized and the color values cited in the Detailed Botanical Description accurately describe the colors of the new *Coreopsis*.

DETAILED BOTANICAL DESCRIPTION

The following is a detailed description of plants three months in age as grown outdoors in one-gallon containers in Kensington, Conn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms from late June until frost in Kensington, Conn.

*Plant type*.—Herbaceous perennial.

*Plant habit*.—Compact, clump-forming, densely branched above ground stems that spread outward.

*Height and spread*.—An average of 33 cm in height and 60 cm in width.

*Cold hardiness*.—At least to U.S.D.A Zone 5a.

*Diseases resistance*.—Has been observed to exhibit resistance to powdery mildew (*Podosphaera macularis*) and leafspot (*Pseudomonas cichorii*).

*Root description*.—Fibrous when young, becoming fleshy with age.

*Propagation*.—Stem cuttings.

*Growth rate*.—Vigorous.

Stem description:

*Shape*.—Rounded to oval, ridged.

*Stem color*.—143A.

*Stem size*.—Main and secondary stems; an average of 20 cm in length and 2 mm in width, tertiary stems; 12 cm in length and 1.7 mm in width.

*Stem surface*.—Glabrous.

*Stem aspect*.—Upright and outward.

*Branching habit*.—Well-branched, an average of 7 main branches, 3 secondary branches per main stem, and 3 tertiary branches.

*Internode length*.—An average of 2 cm.

Foliage description:

*Leaf division*.—Simple.

*Leaf margins*.—Entire.

*Leaf size*.—Variable, up to 7.1 cm in length and 10 mm in width.

*Leaf shape*.—Oblanceolate to ensiform.

*Leaf base*.—Clasping.

*Leaf apex*.—Acute.

*Leaf venation*.—Pinnate, inconspicuous, matches leaf color on upper and lower surface.

*Leaf attachment*.—Sessile.

*Leaf arrangement*.—Opposite.

*Leaf surface*.—Glabrous on upper and lower surface.

*Leaf color*.—Young upper and lower surface; 138A.

Inflorescence description:

*Inflorescence type*.—Composite with a single row of ray florets surrounding disk florets in the center, forming a radiant head, inflorescences are borne on branch terminals in loose corymbs.

*Lastingness of inflorescence*.—8 to 10 days until senescence of ray florets, longer in cool temperatures, bracts and disk florets are persistent.

*Fragrance*.—Faint fragrance.

*Quantity of inflorescences*.—An average of 30 per main branch.

*Inflorescence size*.—Corymbs; an average of 6 cm in height and 12 cm in width, composite; an average of 2 cm in depth and 8 cm in diameter with disk portion 1.6 cm in diameter.

*Inflorescence buds*.—An average of 5 mm in depth and in diameter, flattened globular in shape, color; 143A to 143B with 144A at the top.

*Peduncle*.—An average of 2.5 cm in length and 2.8 mm in width, glabrous surface, 138A.

*Pedicle*.—An average of 6 cm in length and 1.1 mm in width, glabrous surface, 138A in color.

Involucral bracts:

*Bract number*.—8 total, 4 outer bracts and 4 inner bracts.

*Bract arrangement*.—Bracts are un-fused and overlapping surrounding the receptacle in a campanulate form and held close to lower surface of ray florets.

*Bract size*.—Outer and inner bracts; an average of 7 mm in length and 3 mm in width.

*Bract color*.—Inner bracts and outer bracts translucent and 143A to 143C with apex, N144A.

*Bract texture*.—Glabrous on outer and inner surfaces of outer and inner bracts.

*Bract apex*.—Acute on outer and inner bracts.

*Bract base*.—Truncate on inner and outer bracts.

*Bract margins*.—Entire on outer and inner bracts.

*Bract shape*.—Oval to ovate on outer and inner bracts.

Ray florets (sterile):

*Number*.—An average of 7 arranged primarily in one row.

*Shape*.—Oval to oblong.

*Size*.—An average of 3.5 cm in length and 1.5 cm in width.

*Apex*.—2 notched.

*Base*.—Cuneate.

*Margins*.—Entire with apex notched.

*Aspect*.—Held outward to slightly upward.

*Texture*.—Glabrous on upper and lower surface.

*Color*.—When opening and when fully opened upper surface; a blend of 157D and 3A and heavily suffused with 71A towards the base (eye zone) and during cooler growing conditions; the 71A coloration spreads to the entire surface, when opening and when fully opened lower surface; a mix of 1A and 150D.

Disk florets (perfect):

*Shape*.—Tubular, corolla is fused, flared at apex.

*Number*.—About 30.

*Size*.—About 6 mm in length and 1.2 mm in width.

*Color*.—En masse; 7A, corolla tube 154D; with apices 7A to 7B in color.

*Receptacle*.—About 3 mm in diameter and 1 mm in depth, a 145B to 145C in color.

Reproductive organs:

*Presence*.—Disk florets are perfect, ray florets are sterile.

*Gynoecium*.—1 Pistil, 4 mm in length, style is very fine, translucent and 9B in color, 2-lobed stigma is 9A in color, ovary is 1.5 mm in length, 0.5 mm in width, inferior, and 145C in color.

*Androecium*.—5 stamens, fused into tube surrounding style, 2 mm in length and 0.2 mm in width, about 200A to 200B in color, pollen very low in quantity and too low in amount for color coding.

*Fruit/seed*.—No fruit or seed development was observed (nearly sterile).

It is claimed:

1. A new and distinct cultivar of *Coreopsis* plant named 'Starstruck' as herein illustrated and described.

* * * * *